US009297767B2

(12) United States Patent
Maida, Jr. et al.

(10) Patent No.: US 9,297,767 B2
(45) Date of Patent: Mar. 29, 2016

(54) DOWNHOLE SPECIES SELECTIVE OPTICAL FIBER SENSOR SYSTEMS AND METHODS

(75) Inventors: John L. Maida, Jr., Houston, TX (US); Etienne M. Samson, Cypress, TX (US); Rory D. Daussin, Spring, TX (US); Thomas D. Welton, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 308 days.

(21) Appl. No.: 13/253,788

(22) Filed: Oct. 5, 2011

(65) Prior Publication Data

US 2013/0087328 A1 Apr. 11, 2013

(51) Int. Cl.
| G01N 21/78 | (2006.01) |
|---|---|
| E21B 47/12 | (2012.01) |
| G01N 21/77 | (2006.01) |
| G01N 21/80 | (2006.01) |
| E21B 37/06 | (2006.01) |
| E21B 41/02 | (2006.01) |

(52) U.S. Cl.
CPC .............. *G01N 21/78* (2013.01); *E21B 47/123* (2013.01); *G01N 21/7703* (2013.01); *E21B 37/06* (2013.01); *E21B 41/02* (2013.01); *G01N 21/80* (2013.01); *G01N 2021/7716* (2013.01); *G01N 2021/7783* (2013.01)

(58) Field of Classification Search
None
See application file for complete search history.

(56) References Cited

U.S. PATENT DOCUMENTS

| 2,660,887 A | 12/1953 | Frei |
|---|---|---|
| 2,852,693 A | 9/1958 | Hughes et al. |
| 2,868,625 A | 1/1959 | Frank et al. |
| 3,019,841 A | 2/1962 | Ternow et al. |
| 3,282,095 A | 11/1966 | Owens |
| 3,522,685 A | 3/1971 | Zimmerman et al. |
| 3,722,271 A | 3/1973 | Horvitz |
| 4,166,216 A | 8/1979 | Cubberly |

(Continued)

FOREIGN PATENT DOCUMENTS

| EP | 0 072 627 | 2/1983 |
|---|---|---|
| GB | 2368391 | 1/2002 |

(Continued)

OTHER PUBLICATIONS

Fan, Chunfang et al., "Scale Prediction and Inhibition for Unconventional Oil and Gas Production", SPE 130690, SPE International Conference on Oilfield Scale, Aberdeen, United Kingdom, May 26-27, 2010., pp. 1-22.

(Continued)

*Primary Examiner* — Angela M DiTrani
(74) *Attorney, Agent, or Firm* — Krueger Iselin LLP; Scott H. Brown

(57) ABSTRACT

A downhole optical sensor system includes at least one optical sensor positioned in a borehole and coupled to an interface via a fiber optic cable. Each of the optical sensors includes a waveguide for conducting light, and a reagent region positioned between the waveguide and a fluid in the borehole to absorb a portion of the light from the waveguide, the portion being dependent upon a concentration of a chemical species in the fluid. A method for operating a well includes deploying one or more downhole optical sensors in a fluid flow path in the well, probing the one or more downhole optical sensors from a surface interface to detect concentrations of one or more chemical species, and deriving a rate of scale buildup or corrosion based at least in part on the detected concentrations.

18 Claims, 3 Drawing Sheets

(56) References Cited

U.S. PATENT DOCUMENTS

| | | | |
|---|---|---|---|
| 4,785,247 A | 11/1988 | Meador et al. | |
| 4,794,336 A | 12/1988 | Marlow et al. | |
| 4,802,761 A * | 2/1989 | Bowen et al. | 356/301 |
| 4,986,121 A | 1/1991 | Luscombe | |
| 5,037,172 A | 8/1991 | Hekman et al. | |
| 5,351,532 A | 10/1994 | Hager | |
| 5,429,190 A | 7/1995 | Kilgore et al. | |
| 5,626,192 A | 5/1997 | Connell et al. | |
| 5,712,828 A | 1/1998 | Luscombe et al. | |
| 5,729,013 A | 3/1998 | Bergren, III | |
| 5,892,860 A | 4/1999 | Maron et al. | |
| 5,943,293 A | 8/1999 | Luscombe et al. | |
| 6,128,251 A | 10/2000 | Erath et al. | |
| 6,160,762 A | 12/2000 | Luscombe et al. | |
| 6,188,645 B1 | 2/2001 | Maida et al. | |
| 6,188,646 B1 | 2/2001 | Luscombe et al. | |
| 6,195,162 B1 | 2/2001 | Varnham et al. | |
| 6,211,964 B1 | 4/2001 | Luscombe et al. | |
| 6,233,746 B1 | 5/2001 | Skinner | |
| 6,256,588 B1 | 7/2001 | Maida et al. | |
| 6,268,911 B1 | 7/2001 | Tubel et al. | |
| 6,307,809 B1 | 10/2001 | Luscombe et al. | |
| 6,408,943 B1 | 6/2002 | Schultz et al. | |
| 6,422,084 B1 | 7/2002 | Fernald et al. | |
| 6,522,797 B1 | 2/2003 | Siems et al. | |
| 6,561,041 B1 | 5/2003 | Eck | |
| 6,591,025 B1 | 7/2003 | Siems et al. | |
| 6,627,873 B2 | 9/2003 | Tchakarov et al. | |
| 6,731,389 B2 | 5/2004 | Luscombe et al. | |
| 6,789,621 B2 | 9/2004 | Wetzel et al. | |
| 6,834,233 B2 | 12/2004 | Economides et al. | |
| 6,847,034 B2 | 1/2005 | Shah et al. | |
| 6,853,604 B2 | 2/2005 | Spackman et al. | |
| 6,891,606 B2 * | 5/2005 | Smith et al. | 356/70 |
| 6,907,170 B1 | 6/2005 | Maida | |
| 6,913,083 B2 | 7/2005 | Smith | |
| 6,931,188 B2 | 8/2005 | Kersey et al. | |
| 6,939,717 B2 * | 9/2005 | Jiang et al. | 436/121 |
| 6,957,574 B2 | 10/2005 | Ogle | |
| 7,006,918 B2 | 2/2006 | Economides et al. | |
| 7,028,773 B2 | 4/2006 | Fujisawa et al. | |
| 7,095,012 B2 | 8/2006 | Fujisawa et al. | |
| 7,104,324 B2 | 9/2006 | Wetzel et al. | |
| 7,159,468 B2 | 1/2007 | Skinner et al. | |
| 7,163,055 B2 | 1/2007 | Coon et al. | |
| 7,182,134 B2 | 2/2007 | Wetzel et al. | |
| 7,216,710 B2 | 5/2007 | Welton et al. | |
| 7,219,729 B2 | 5/2007 | Bostick, III et al. | |
| 7,219,730 B2 | 5/2007 | Tilton et al. | |
| 7,245,791 B2 | 7/2007 | Rambow et al. | |
| 7,408,645 B2 | 8/2008 | DiFoggio | |
| 7,409,858 B2 | 8/2008 | Dria et al. | |
| 7,458,273 B2 | 12/2008 | Skinner et al. | |
| 7,461,547 B2 | 12/2008 | Terabayashi et al. | |
| 7,511,823 B2 | 3/2009 | Schultz et al. | |
| 7,529,434 B2 | 5/2009 | Taverner et al. | |
| 7,641,395 B2 | 1/2010 | Ringgenberg et al. | |
| 7,665,543 B2 | 2/2010 | Bostick, III et al. | |
| 7,669,440 B2 | 3/2010 | Kersey et al. | |
| 7,733,490 B2 | 6/2010 | Goodwin et al. | |
| 7,864,321 B2 * | 1/2011 | Caron et al. | 356/432 |
| 7,938,178 B2 | 5/2011 | Ringgenberg et al. | |
| 8,104,338 B2 | 1/2012 | DiFoggio | |
| 8,230,916 B2 | 7/2012 | Sumrall et al. | |
| 8,447,529 B2 * | 5/2013 | Hernandez et al. | 702/25 |
| 8,831,388 B2 * | 9/2014 | Boersma | G01N 21/774 385/147 |
| 8,908,165 B2 | 12/2014 | Tunheim et al. | |
| 2003/0205375 A1 | 11/2003 | Wright et al. | |
| 2003/0210403 A1 | 11/2003 | Luscombe et al. | |
| 2005/0072678 A1 | 4/2005 | Hunter et al. | |
| 2005/0169794 A1 | 8/2005 | Welton et al. | |
| 2005/0207279 A1 | 9/2005 | Chemali et al. | |
| 2005/0263281 A1 * | 12/2005 | Lovell et al. | 166/255.1 |
| 2006/0010973 A1 | 1/2006 | Brown | |
| 2006/0081412 A1 | 4/2006 | Wright et al. | |
| 2007/0010404 A1 | 1/2007 | Welton et al. | |
| 2007/0187648 A1 | 8/2007 | Welton et al. | |
| 2007/0193351 A1 | 8/2007 | DiFoggio | |
| 2008/0227668 A1 | 9/2008 | Welton et al. | |
| 2008/0227669 A1 | 9/2008 | Welton | |
| 2008/0280789 A1 | 11/2008 | Welton et al. | |
| 2008/0314139 A1 | 12/2008 | DiFoggio | |
| 2009/0120640 A1 | 5/2009 | Kulakofsky et al. | |
| 2009/0143258 A1 | 6/2009 | Welton et al. | |
| 2009/0271115 A1 | 10/2009 | Davis et al. | |
| 2010/0177310 A1 * | 7/2010 | DiFoggio | 356/326 |
| 2010/0269579 A1 * | 10/2010 | Lawrence et al. | 73/152.23 |
| 2011/0090496 A1 | 4/2011 | Samson et al. | |
| 2011/0100629 A1 | 5/2011 | Welton et al. | |
| 2011/0105368 A1 | 5/2011 | Welton et al. | |
| 2011/0109912 A1 | 5/2011 | Spross et al. | |
| 2011/0116099 A1 | 5/2011 | Spross et al. | |
| 2011/0280103 A1 * | 11/2011 | Bostick, III | E21B 47/101 367/35 |
| 2012/0257475 A1 * | 10/2012 | Luscombe | G01V 1/48 367/25 |
| 2013/0031970 A1 | 2/2013 | Freese et al. | |
| 2013/0245947 A1 | 9/2013 | Samsom et al. | |
| 2013/0332130 A1 | 12/2013 | Loveless et al. | |

FOREIGN PATENT DOCUMENTS

| | | |
|---|---|---|
| GB | 2 445 209 | 2/2008 |
| WO | WO-98/57030 | 12/1998 |
| WO | WO-01/81914 | 11/2001 |
| WO | WO-2006/063094 | 6/2006 |
| WO | WO-2008/081467 | 7/2008 |
| WO | WO-2011/193401 | 2/2011 |
| WO | WO-2013/052891 A3 | 4/2013 |
| WO | WO-2013/137992 | 9/2013 |

OTHER PUBLICATIONS

Kohler, N. et al., "Static and Dynamic Evaluation of Calcium Carbonate Scale Formation and Inhibition", SPE 68963, SPE European Formation Damage Conference, The Hague, The Netherlands, May 21-22, 2001, p. 1-11.

Nancollas, G. H., et al., "The Kinetics of Crystallization of Scale-Forming Minerals", SPE 4360, Apr. 1974, 10 pages.

IEEE, "IEEE Standard for Long Wavelength Wireless Network Protocol", *IEEE* Std 1902.1, New York, NY, (Mar. 31, 2009), 35 pgs.

Graber, Karen K., et al., "Drill String Tool Sheet", *Overview of Ocean Drilling Program*, http://www.odp.tamu.edu/publications/tnotes/tn31/drill_s/drill_s.htm>.(retrieved Sep. 21, 2009), (Jul. 2004), pp. 1-3.

Thompson Reuters, "RuBee, High-Security, Harsh-Environment RFID Alternative", http://www.reuters.com/article/pressRelease/idUS260082+11-Feb-2009+BW20090211>; (retrieved Sep. 21, 2009), (Feb. 11, 2009), pp. 1-2.

Li, Weizhuo et al., "Wavelength Multiplexing of Microelectromechanical System Pressure and Temperature Sensors Using Fiber Bragg Gratings and Arrayed Waveguide Gratings", *Opt. Eng. Society of Photo-Optical Instrumentation Engineers*, 0091-3286/2003, (Feb. 2003), pp. 431-438.

Tudor, M.J. et al., "Silicon Resonator Sensors: Interrogation Techniques and Characteristics", *IEE Proceedings*, vol. 135, Pt. D, No. 5, (Sep. 1988), pp. 364-368.

"PCT International Search Report and Written Opinion", dated Sep. 29, 2009, Appl No. PCT/US2009/053492, A Near-Field Electromagnetic Communications Network for Downhole Telemetry, filed Aug. 11, 2009, 7 pgs.

"PCT International Preliminary Report on Patentability", dated Sep. 26, 2013, Appl No. PCT/US2012/059091, "Downhole Species Selective Optical Fiber Sensor Systems and Methods", filed Oct. 5, 2012, 27 pgs.

"PCT International Search Report and Written Opinion", dated Apr. 4, 2013, Appl No. PCT/US2012/059091, "Downhole Species Selective Optical Fiber Sensor Systems and Methods", filed Oct. 5, 2012, 27 pgs.

(56) References Cited

OTHER PUBLICATIONS

"US Application", dated Mar. 13, 2012, U.S. Appl. No. 13/418,455, "Downhole Systems and Methods for Water Source Determination", filed Mar. 13, 2012, 24 pgs.
Angelidis, Diogenes et al., "Optical Micromachined Pressure Sensor for Aerospace Applications", Optical Engineering, vol. 31, No. 8, (Aug. 1992), pp. 1636-1642.
Aratani, K. "Process and Design Considerations for Surface Micromachined Beams for a Tuneable Interferometer Array in Silicon", IEEE Xplore, IEEE, 1993, pp. 230-235.
Burns, D. W., et al., "Thin Films for Micromechanical Sensors", J. Vac. Sci. Technol. A 8(4), American Vacuum Society, (Jul. 1990), pp. 3606-3613.
Fan, Chunfang et al., "Scale Prediction and Inhibition for Unconventional Oil and Gas Production", SPE 130690, SPE International Conference on Oilfield Scale, Aberdeen, United Kingdom, May 26-27, 2010, pp. 1-22.
Halliburton Energy Services, Inc, "StimWatch Stimulation Monitoring Service—FiberWatch Fiber Optic Distributed Temperature Sensing Technology", Pinnacle, a Halliburton Services, http://www.halliburton.com/public/pe/contents/Data_Sheets/web/H/H04481.pdf, 2010, pp. 1-4.
Hirschfeld, Tomas et al., "Feasibility of using fiber optics for monitoring groundwater contaminants", Optical Engineering XP-002692941, vol. 22 No. 5, Sep.-Oct. 1983, pp. 527-531.
Johnson, R. L., et al., "Miniature Instrument for the Measurement of Gap Thickness Using Poly-Chromatic Interferometry", Center for Astronomical Adaptive Optics, Steward Observatory, The University of Arizona, Tucson, AZ, 9 pgs.
Kan, Amy T., et al., "Scale Prediction for Oil and Gas Production", SPE 132237, CPS/SPE International Oil & Gas Conference and Exhibition in China held in Beijing, China Jun. 8-10, 2010, 29 pages.
Kohler, N. et al., "Static and Dynamic Evaluation of Calcium Carbonate Scale Formation and Inhibition", SPE 68963, SPE European Formation Damage Conference, The Hague, The Netherlands, May 21-22, 2001, pp. 1-11.
MacDougall, Trevor W., et al., "Large Diameter Waveguide Bragg Grating Components and Their Application in Downhole Oil & Gas Sensing", Weatherford International, Wallingford, CT, 12 pgs.
Martins-Filho, Joaquim F., et al., "Optical Fibre Sensor System for Multipoint Corrosion Detection", Optical Fiber New Developments, Christophe Lethien (Ed.), ISBN: 978-953-7619-50-3, InTech, DOI: 10.5772/7579. Available from: http://www.intechopen.com/books/optical-fiber-new-developments/optical-fibre-sensor-system-for-multipoint-corrosion-detection, (Dec. 1, 2009), pp. 36-42.
Nancollas, G. H., et al., "The Kinetics of Crystallization of Scale-Forming Minerals", SPE 4360, Apr. 1974, 10 pgs.
Pitcher, R. J., et al., "Optothermal Drive of Silicon Resonators: The Influence of Surface Coatings", Sensors and Actuators, A21-23, (1990), pp. 387-390.
Putty, Michael W., et al., "Process Integration for Active Polysilicon Resonant Microstructures", Sensors and Actuators, 20, (1989), pp. 143-151.
Ravi, Kris et al., "Cement Slurry Monitoring", U.S. Appl. No. 13/028,542, filed Feb. 16, 2011, (Aug. 16, 2012), 19 pgs.
Samson, Etienne et al., "A Near-Field Electromagnetic Communications Network for Downhole Telemetry", PCT Appl No. US09/53492, filed Aug. 11, 2009, 15 pgs.
Shell, Baker Hughes, "Pioneer Real-time Compaction Imaging System", Oil&Gas Eurasia, http://www.oilandgaseurasia.com/news/p/2/news/5146, Jun. 29, 2009, 2 pgs.
Stiff, Henry A., et al., "A Method for Predicting the Tendency of Oil Field Waters to Deposit Calcium Carbonate", Petroleum Transactions, AIME, vol. 195, 1952, pp. 213-216.
Tseng, Fan-Gang et al., "Polymer MEMS-Based Fabry-Perot Shear Stress Sensor", IEEE Sensors Journal, vol. 3, No. 6, (Dec. 2003), pp. 812-817.
Unknown, "Optical Activation of a Silicon Vibrating Sensor", Electronic Letters, vol. 22, No. 21, (Oct. 9, 1986), pp. 1097-1099.
"Search report and written opinion", Jan. 16, 2014, PCT Appl No. PCT/US2013/024845, "Downhole System and Methods for Water Source Determination," filed Feb. 6, 2013, 12 pgs.
Medhat, Abdou et al., "Finding Value in Formation Water", Oilfield Review, vol. 23, No. 1, Mar. 1, 2011, XP055095547, ISSN: 0923-1730, 12 pgs.
"International Preliminary Report on Patentability", Dated Jun. 23, 2014, Appl No. PCT/US2013/024845, "Downhole system and methods for water source determination," filed Feb. 6, 2013, 9 pgs.
"AU Patent Examination Report No. 1", dated Jun. 3, 2015, Appl No. 2013232590, "Downhole Systems and Methods for Water Source Determination," filed Feb. 6, 2013, 4 pgs.
"US Non Final Office Action", dated Apr. 23, 2015, U.S. Appl. No. 13/418,455, "Downhole Systems and Methods for Water Source Determination," filed Mar. 13, 2012, 26 pgs.
Dessy, Raymond E., "Waveguides as Chemical Sensors", Analytical Chemistry, vol. 61, No. 19, Oct. 1, 1989, pp. 1079A-1094A, ACS Publications, Washington, DC, 14 pgs.

* cited by examiner

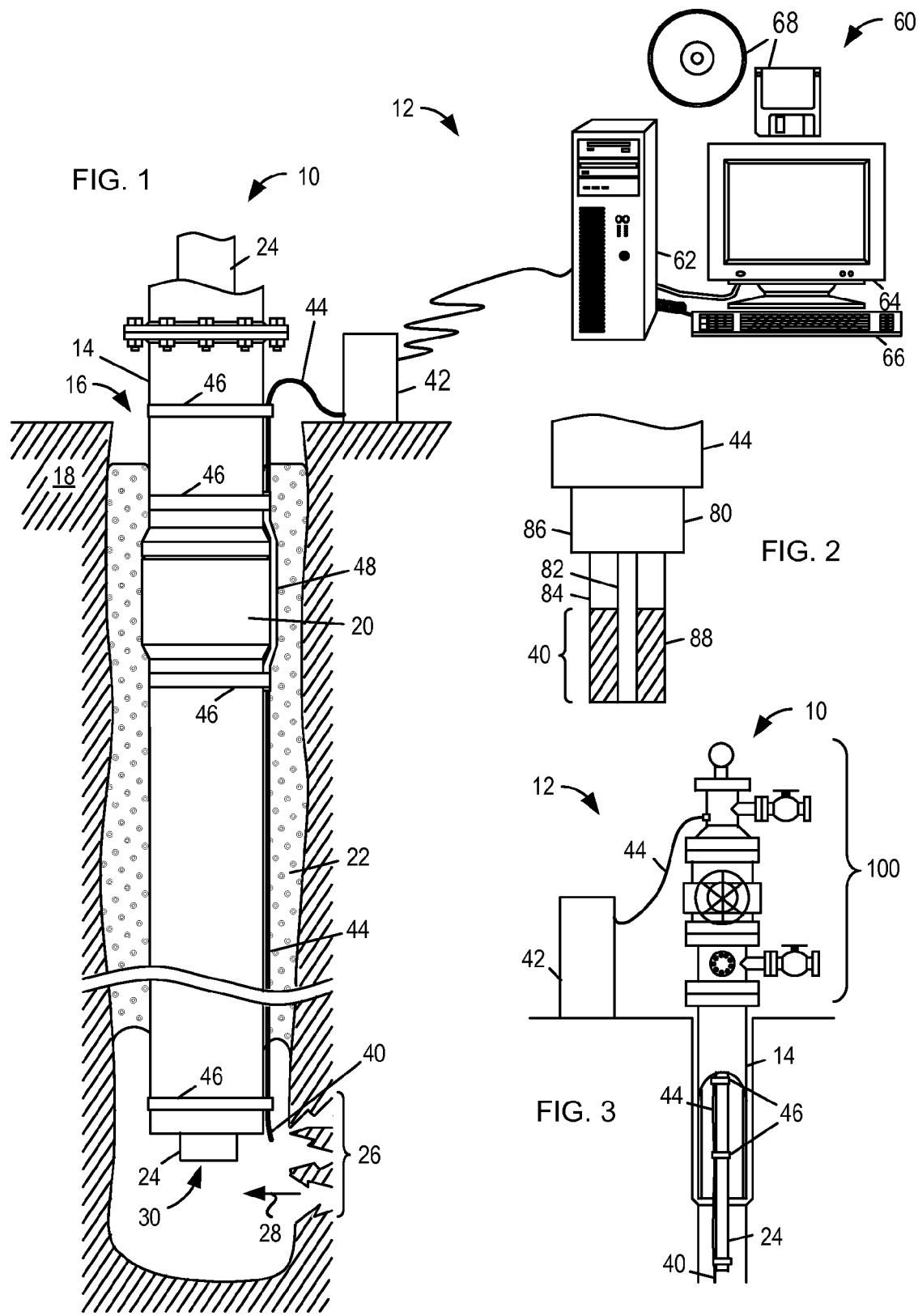

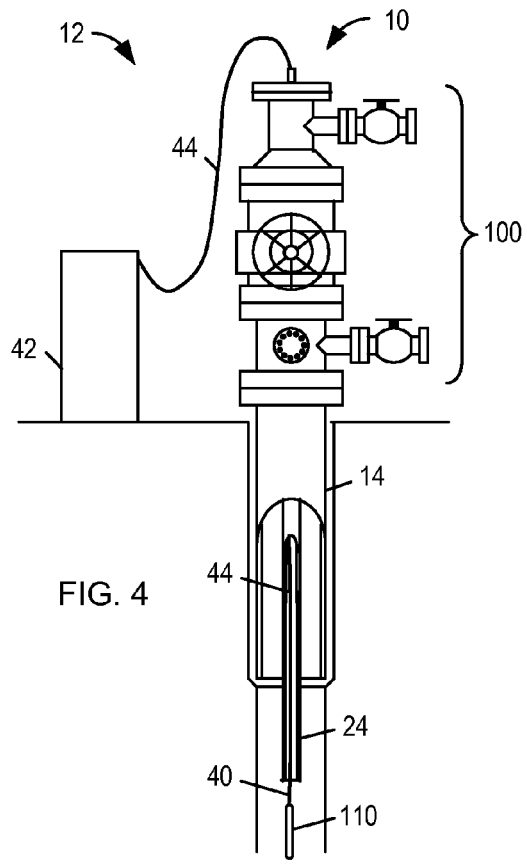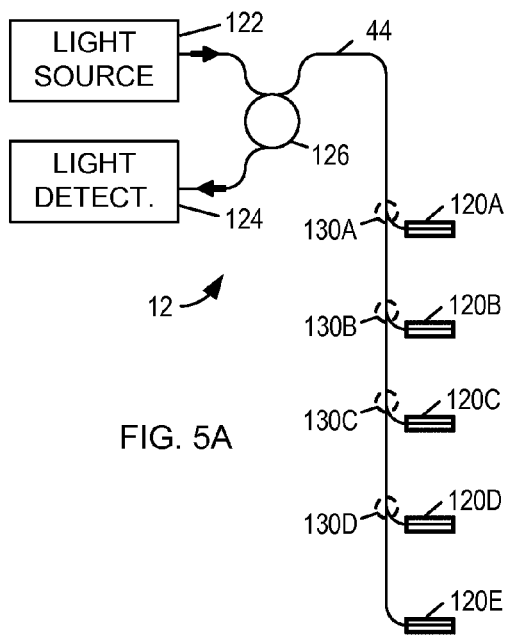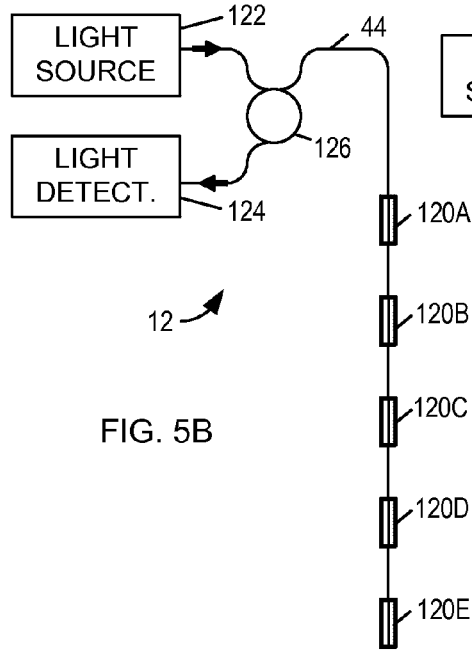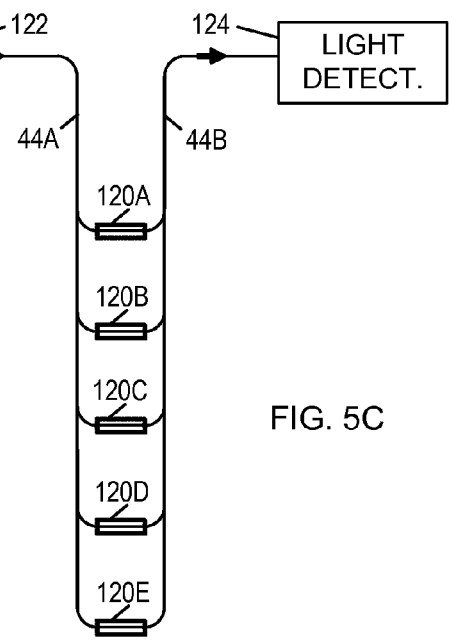
FIG. 4
FIG. 5A
FIG. 5B
FIG. 5C

DOWNHOLE SPECIES SELECTIVE OPTICAL FIBER SENSOR SYSTEMS AND METHODS

BACKGROUND

In oil and gas production wells, scale formation is a significant issue. As used herein, the term "scale" refers to deposits or coatings formed on borehole tubulars and components. Produced water includes formation water that is often saturated with mineral ions. During well operation, formation water may mix with water from other zones, injected water from injection wells, or other injected materials that may have different ionic species. This mixing of incompatible water, along with changes in temperature or pressure, often results in the development of scale. Common scales include calcium carbonate, calcium sulfate, barium sulfate, strontium sulfate, iron sulfide, zinc sulfide, iron carbonate, iron oxides, and barium strontium sulfate. Scale builds up on the surfaces of borehole tubulars and/or components in contact with produced water, impeding fluid flow. If no countermeasures are taken, the borehole tubulars and/or components may become completely blocked over time.

Corrosion is also a large concern in oil and gas production wells. As used herein, the term "corrosion" refers to a loss of metal due to chemical or electrochemical reactions. Borehole tubulars and components are typically made of steel, an alloy consisting mostly of iron. When iron is in contact with water containing dissolved oxygen, sulfur dioxide, and/or carbon dioxide, iron hydroxide species can form on the surface of the iron. Similarly, when iron is in contact with water containing dissolved carbon dioxide and hydrogen sulfide, iron sulfide species can form on the iron surface. As the iron hydroxide or iron sulfide species flake off from the surface, fresh iron is exposed. This corrosion process continues until either all of the iron is consumed, or until one of the reactant species is removed or consumed. Corrosion products that accumulate such as iron hydroxide and iron sulfide may also be considered as scale.

Inhibitors are often periodically circulated through the various flow paths of a well to prevent or reduce scaling and/or corrosion. However, such inhibitors are often unnecessary or are overused as a precautionary measure due to a lack of knowledge about the precise conditions downhole.

BRIEF DESCRIPTION OF THE DRAWINGS

A better understanding of the various disclosed embodiments can be obtained when the detailed description is considered in conjunction with the attached drawings, in which:

FIG. 1 is a side elevation view of an illustrative downhole optical sensor system in a production well;

FIG. 2 is a diagram of an illustrative fiber optic cable and optical sensing system;

FIGS. 3-4 show alternative downhole optical sensor system embodiments;

FIGS. 5A-5C show illustrative distributed downhole species sensing techniques.

Figure 6:
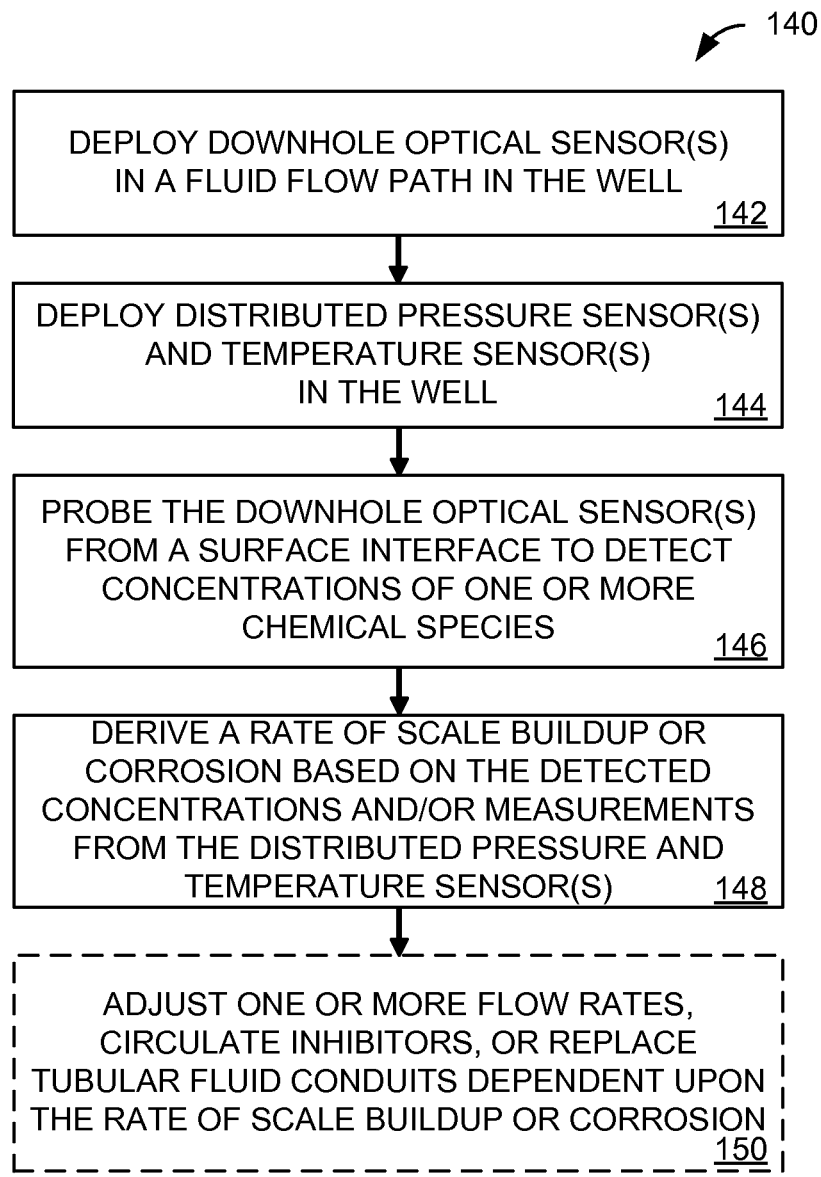
FIG. 6 is a flowchart of an illustrative method for operating a well.

While the invention is susceptible to various alternative forms, equivalents, and modifications, specific embodiments thereof are shown by way of example in the drawings and will herein be described in detail. It should be understood, however, that the drawings and detailed description thereto do not limit the disclosure, but on the contrary, they provide the foundation for alternative forms, equivalents, and modifications falling within the scope of the appended claims.

DETAILED DESCRIPTION

The problems outlined above are at least in part addressed by the disclosed systems and methods that employ downhole optical sensors for ion and/or chemical concentrations. At least some described downhole optical sensor system embodiments include one or more optical sensors positioned in a borehole and coupled to a surface interface via a fiber optic cable. Each of the optical sensors includes a waveguide for conducting light and a reagent region positioned between the waveguide and a fluid in the borehole to absorb a portion of the light from the waveguide, the portion being dependent upon a concentration of a chemical species in the fluid. (As the term "chemical species" is used herein, it encompasses any constitutionally or isotopically distinct atom, molecule, ion, radical, or complex.)

Turning now to the figures, FIG. 1 shows a well 10 equipped with an illustrative embodiment of a downhole optical sensor system 12. The well 10 shown in FIG. 1 has been constructed and completed in a typical manner, and it includes a casing string 14 positioned in a borehole 16 that has been formed in the earth 18 by a drill bit. The casing string 14 includes multiple tubular casing sections (usually about 30 foot long) connected end-to-end by couplings. One such coupling is shown in FIG. 1 and labeled '20'. Within the well 10, cement 22 has been injected between an outer surface of the casing string 14 and an inner surface of the borehole 16 and allowed to set. A production tubing string 24 has been positioned in an inner bore of the casing string 14.

The well 10 is adapted to guide a desired fluid (e.g., oil or gas) from a bottom of the borehole 16 to a surface of the earth 18. Perforations 26 have been formed at a bottom of the borehole 16 to facilitate the flow of a fluid 28 from a surrounding formation (i.e., a "formation fluid") into the borehole and thence to the surface via an opening 30 at the bottom of the production tubing string 24. Note that this well configuration is illustrative and not limiting on the scope of the disclosure.

As is typical, a majority of the components of the casing string 14 are made of steel, an alloy consisting mostly of iron. During operation of the well 10, the formation fluid flow carries a certain amount of water into the borehole and along the fluid flow path to the surface. This "produced water" often includes chemical species that cause scale buildup and/or corrosion in those components of the casing string 14 that are in contact with the formation fluid 28. As described in more detail below, the downhole optical sensor system 12 is adapted to detect concentration(s) of one or more chemical species in the formation fluid 28.

The detected chemical species may be, for example, known to cause scale buildup and/or corrosion on one or more metal surfaces of the casing string 14. Alternatively, or in addition, the detected chemical species may be representative of one or more scale inhibitor substance(s) or compound(s) introduced into the formation fluid 28 to combat scale buildup on one or more metal surfaces of the casing string 14, or by one or more corrosion inhibitor substance(s) or compound(s) introduced into the formation fluid 28 to combat corrosion on one or more metal surfaces of the casing string 14.

In the embodiment of FIG. 1, the downhole optical sensor system 12 includes an optical sensor 40 in contact with the formation fluid 28 at the bottom of the borehole 16 and coupled to an interface 42 via a fiber optic cable 44. The interface 42 is located on the surface of the earth 18 near the wellhead, i.e., a "surface interface". The optical sensor 40 includes a waveguide and is adapted to alter light passing through the waveguide dependent upon a concentration of one or more chemical species in the formation fluid 28.

In the embodiment of FIG. 1, the fiber optic cable 44 extends along an outer surface of the casing string 14 and is held against the outer surface of the of the casing string 14 at spaced apart locations by multiple bands 46 that extend around the casing string 14. A protective covering may be installed over the fiber optic cable 44 at each of the couplings of the casing string 14 to prevent the cable from being pinched or sheared by the coupling's contact with the borehole wall. In FIG. 1, a protective covering 48 is installed over the fiber optic cable 44 at the coupling 20 of the casing string 14 and is held in place by two of the bands 46 installed on either side of coupling 20.

In at least some embodiments, the fiber optic cable 44 terminates at surface interface 42 with an optical port adapted for coupling the fiber optic cable to a light source and a detector. The light source transmits light along the fiber optic cable to the optical sensor 40, which alters the light to provide some indication of a given chemical species concentration. The optical sensor 40 returns light along the fiber optic cable to the surface interface 42 where the optical port communicates it to the detector. The detector responsively produces an electrical output signal indicative of the concentration of the given chemical species in the formation fluid 28. The optical port may be configured to communicate the downgoing light signal along one or more optical fibers that are different from the optical fibers carrying the return light signal, or may be configured to use the same optical fibers for communicating both light signals.

The illustrative downhole optical sensor system 12 of FIG. 1 further includes a computer 60 coupled to the surface interface 42 to control the light source and detector. The illustrated computer 60 includes a chassis 62, an output device 64 (e.g., a monitor as shown in FIG. 1, or a printer), an input device 66 (e.g., a keyboard), and information storage media 68 (e.g., magnetic or optical data storage disks). However, the computer may be implemented in different forms including, e.g., an embedded computer permanently installed as part of the surface interface 42, a portable computer that is plugged into the surface interface 42 as desired to collect data, a remote desktop computer coupled to the surface interface 42 via a wireless link and/or a wired computer network, a mobile phone/PDA, or indeed any electronic device having a programmable processor and an interface for I/O. The computer 60 is adapted to receive the electrical output signal produced by the surface interface 42 and to responsively determine a rate or accumulation of scale buildup on one or more components of the casing string 14, a corrosion rate or total loss due to corrosion occurring on one or more components of the casing string 14, and/or an estimated useful life of one or more components of the casing string 14 subject to scale buildup and/or corrosion. In at least some embodiments, a computer coupled to an interface obtains measurements indicative of a chemical species concentration, the computer having software that configures one or more processors to determine, based at least in part on the measurements, at least one of: a rate of scale buildup, a corrosion rate, quantity of scale, corrosion loss, and an estimated useful life.

For example, the information storage media 68 may store a software program for execution by computer 60. The instructions of the software program may cause the computer 60 to collect information regarding downhole conditions including, e.g., a given chemical species concentration derived from the electrical signal from surface interface 42 and, based at least in part thereon, to determine the rate of scale buildup on the one or more components of the casing string 14, the rate of corrosion occurring on the one or more components of the casing string 14, and/or the estimated useful life of the one or more components of the casing string 14 subject to scale buildup and/or corrosion. The instructions of the software program may also cause the computer 60 to communicate to the user the rate of scale buildup, the corrosion rate, and/or the estimated useful life via the output device 64. Note that the scaling/corrosion information can be communicated via a graphical output device, via email or SMS text, via an audible or visual alarm indicator, or indeed by any suitable output technique.

The software program executed by the computer 60 may, for example, embody a model for predicting the rate of scale buildup, the corrosion rate, and/or the estimated useful life. Several suitable models are known in the oil and gas production industry. See, for example, "A Method for Predicting the Tendency of Oil Field Waters to Deposit Calcium Carbonate" by H. Stiff and L. E. Davis, Petroleum Transactions AIME, Vol. 195, 1952, pp. 213-216; "Scale Prediction for Oil and Gas Production" by Amy T. Kan and Mason B. Tomson, Society of Petroleum Engineers Paper No. 132237, International Oil and Gas Conference and Exhibition in China, 8-10 Jun. 2010, Beijing, China; and "Validation of Scale Prediction Algorithms at Oilfield Conditions" by Amy T. Kan et al., Society of Petroleum Engineers Paper No. 93264, 2005 SPE International Symposium on Oilfield Chemistry, Houston, Tex., 2-4 Feb. 2005. The model employed by the software program may, for example, use the measurements of the concentrations of the one or more chemical species in the formation fluid 28, along with measurements of temperatures and/or pressures of the formation fluid 28 along its flow path, to predict the rate of scale buildup, the corrosion rate, and/or the estimated useful life.

FIG. 2 is a diagram of an illustrative embodiment of the fiber optic cable 44 and optical sensor 40. In the embodiment of FIG. 2, fiber optic cable 44 includes at least one optical fiber 80 that can be exposed by pulling back the cable sheath. The optical fiber 80 includes a substantially transparent inner core 82 surrounded by a substantially transparent cladding layer 84 having a higher index of refraction, which causes the inner core 82 to serve as a waveguide. The cladding layer 84 is in turn surrounded by one or more protective layers 86 that prevents external gasses from degrading the performance of the optical fiber.

The optical fiber 80 is provided with a sensing region 88 that, at least in some embodiments, is an exposed portion of the cladding layer 84 that may be further enhanced with a reagent designed to complex with a given chemical species in solution. The reagent region 88 of the optical sensor 40 surrounds the inner core 82 (i.e., the waveguide) and is in direct contact with both the waveguide and the formation fluid 28 (see FIG. 1). The reagent region 88 may include, for example, a reagent changes color (i.e., changes its light absorption spectrum) when it complexes with a chemical species in solution. The reagent may be or include, for example, a chromoionophore that complexes with ions of barium, calcium, iron, lead, magnesium, phosphorus, potassium, sodium, strontium, zinc, and/or sulfur oxyanion. The reagent may be suspended in a medium that confines the reagent to the reagent region 88, yet enables the given chemical species to diffuse to or from the surrounding fluid in accordance with the concentration in that fluid.

Within the optical sensor 40, a portion of the light passing through the inner core 82 (i.e., the waveguide) of the optical sensor 40 expectedly interacts with the reagent region 88. When the reagent complexes with a chemical species in the formation fluid 28, the complexes may more strongly or more weakly absorb the particular wavelength of light traveling through the reagent region 88. As a result, the intensity of the light exiting the optical sensor 40 may be reduced dependent upon the concentration of the chemical species in the formation fluid 28. Again, the chemical species may be chosen based on its ability to cause or indicate scale buildup and/or corrosion. Alternatively, or in addition, the chemical species may be chosen based on its ability to inhibit scale or corrosion or in some fashion indicate the presence of inhibitor substance(s) or compound(s) introduced into the fluid flow.

In at least some embodiments of the downhole optical sensor system 12, the light source in the surface interface 42 provides pulses of light via the optical port to the optical fiber 80 of the fiber optic cable 44. The light has, or includes, one or more wavelengths that are absorbed in the reagent region 88 of the optical sensor 40 when the reagent complexes with a selected chemical species in the formation fluid 28. The light may be or include, for example, near infrared light. When a light pulse reaches the optical sensor 40, the light passes through the optical sensor 40 and is altered (e.g., attenuated) within the reagent region 88 by an amount dependent on the concentration of the selected chemical species in the formation fluid 28.

The light traveling through the optical sensor 40 may be routed back to the surface along a different optical fiber in cable 44. In the illustrated embodiment, however, the light traveling through the optical sensor 40 reaches an end of the inner core 82, which is polished or mirrored to reflect a substantial portion of the light incident on it. The reflected light travels back through the optical sensor 40 on its way to the surface interface 42. During the return trip through the optical sensor, the light pulse is further altered (e.g., attenuated) within the reagent region 88 dependent upon the concentration of the selected chemical species in the formation fluid 28. The reflected pulse of light then travels back through the optical fiber 80 of the fiber optic cable 44 to the surface interface 42. A light detector in the surface interface 42 receives the reflected pulse of light and produces the electrical output signal indicative of the concentration of the selected chemical species in the formation fluid 28. For example, the detected intensity of the received light pulse at a given frequency may be proportional to the concentration of the given species. Alternatively, the detected intensity may be a nonlinear function of the transmitted light intensity and the concentration of the given species, but the surface interface or the computer is provided with sufficient information to derive the desired concentration measurement.

FIG. 3 shows an alternative embodiment of downhole optical sensor system 12 having the fiber optic cable 44 strapped to the outside of the production tubing 24 rather than the outside of casing 14. Rather than exiting the well 10 from the annular space outside the casing, the fiber optic cable 44 exits through an appropriate port in the "Christmas tree" 100, i.e., the assembly of valves, spools, and fittings connected to the top of the well to direct and control the flow of fluids to and from the well. The fiber optic cable 44 extends along the outer surface of the production tubing string 24 and is held against the outer surface of the of the production tubing string 24 at spaced apart locations by multiple bands 46 that extend around the production tubing string 24. As in the embodiment of FIG. 1, the downhole optical sensor system 12 of FIG. 3 includes an optical sensor 40 in contact with formation fluid at the bottom of a borehole and coupled to the surface interface 42 via the fiber optic cable 44.

FIG. 4 shows another alternative embodiment of downhole optical sensor system 12 having the fiber optic cable 44 suspended inside production tubing 24. A weight 110 or other conveyance mechanism is employed to deploy and possibly anchor the fiber optic cable 44 within the production tubing 24 to minimize risks of tangling and movement of the cable from its desired location. The optical sensor 40 may be positioned at the bottom of the well near weight 110. The fiber optic cable 44 exits the well via an appropriate port in Christmas tree 100 and attaches to the surface interface 42.

Other alternative embodiments employ composite tubing with one or more optical fibers embedded in the wall of the tubing. The composite tubing can be employed as the casing and/or the production string. In either case, a coupling or terminator can be provided at the end of the composite tubing to couple an optical sensor 40 to the embedded optical fiber. In still other embodiments, the light source and/or light detector may be positioned downhole and coupled to the surface interface 42 via electrical conductors.

The well 10 illustrated in FIGS. 1 and 3-4 offers two potential flow paths for fluid to move between the surface and the bottom of the well. The first, and most commonly employed, is the interior of the production tubing. The second is the annular space between the production tubing and the casing. Usually the outermost annular space (outside the casing) is sealed by cement for a variety of reasons usually including the prevention of any fluid flow in this space. Usually, the point at which it is most desirable to measure concentrations of potential scaling and corrosion agents will be the point at which formation fluid enters the borehole, i.e., the completion zone, or points of potential constriction, e.g., where the fluid enters the flow path and any branches, chokes, or valves along the flow path. Often, one optical sensor 40 will be sufficient, and it can be located at the end of the fiber optic cable 44 in one of the deployments described previously.

However, other well configurations are known that have a substantial number of flow paths, particularly wells designed to produce from multiple completion zones. It may be desirable to provide multiple optical sensors 40 so as to be able to individually monitor each fluid flow. Moreover, it may be desirable to provide multiple optical sensors along a given fluid flow path, as such a well configuration may create atypical pressure and temperature changes along the flow path and, in some cases, mixing with other fluid flows. While it is possible to provide such sensors by providing a separate fiber optic cable for each optical sensor, it will be in many cases more efficient to provide a single fiber optic cable with multiple sensors.

FIGS. 5A-5C show various illustrative downhole optical sensor system 12 embodiments that provide multiple sensors for a given fiber optic cable. FIGS. 5A-5C show multiple spaced-apart optical sensors 120A-120E, referred to collectively as the optical sensors 120. Placed in contact with a formation fluid each of the optical sensors 120 may be adapted to alter light passing therethrough dependent upon a concentration of one or more chemical species in the formation fluid (e.g., in a fashion similar to the optical sensor 40 of FIG. 2). Other ones of the optical sensors 120 may be adapted to alter light passing therethrough dependent upon a concentration of hydrogen ions in the formation fluid to indicate a pH of the formation fluid. Still other ones of the optical sensors 120 may be adapted to alter light passing therethrough dependent upon a temperature or a pressure of the formation fluid.

In the embodiment of FIG. 5A, the surface interface 42 for the downhole optical sensor system 12 includes a light source 122, a light detector 124, and an optical circulator 126 that couples the source and detector to fiber optic cable 44. Optical splitters 130A-130D couple the optical fiber to corresponding optical sensors 120A-120D, and a last optical sensor 120E may be coupled to the terminal end of the optical fiber. The optical circulator 126 routes pulses of light from light source 122 to the optical fiber in fiber optic cable 44. Each pulse of light propagates along the optical fiber to the series of optical splitters 130A-130D. Each splitter directs a portion of the light (e.g., 2%) to the corresponding sensor and passes the remainder of the light along the cable 44. Each optical sensor 120A-120E alters (e.g., attenuates) the light in accordance with the concentration of the selected chemical species and reflects back the altered light. The optical splitters 130A-130D recombine the reflected light into a single beam propagating upward along the fiber optic cable 44. Due to the travel-time differences, the light propagating upward now consists of a series of pulses, the first pulse corresponding to the first sensor 120A, the second pulse corresponding to the second sensor 120B, etc. The optical circulator 126 directs these pulses to the light detector 124 which determines a sensor measurement for each pulse.

Where the fiber optic cable 44 includes multiple optical fibers or multi-stranded optical fibers, the optical sensors 120A-120E can be directly coupled to different ones of the optical fibers or strands. The optical splitters would not be needed in this variation. The detector 124 can be coupled to measure the total light returned along the multiple fibers or strands, as the travel time difference to the various sensors will convert the transmitted light pulse into a series of reflected light pulses, with each pulse representing a corresponding optical sensor measurement.

In the embodiment of FIG. 5B, the downhole optical sensor system 12 also includes the light source 122, the light detector 124, and the optical circulator 126 as before. The optical sensors 120 are positioned in series along the fiber optic cable 44. Each of the optical sensors 120 is adapted to alter (e.g., attenuate) light in a distinct range of wavelengths (i.e., band of frequencies) such that the optical sensors 120 alter light in different wavelength ranges (i.e., frequency bands) while leaving the other wavelengths largely unaffected.

The light source 122 may produce light having components in each of the wavelength ranges corresponding to the optical sensors 120. As the light propagates along the fiber optic cable and through the optical sensors 120, each of the optical sensors alter the light components within their associated wavelength range. In the illustrated embodiment, the light reflects from the end of the cable and propagates back to the surface, passing a second time through each of the sensors which further alter (e.g., attenuate) the light component in their associated wavelength range. When the reflected light reaches the surface interface, the optical circulator 126 directs the reflected light to the light detector 124, which analyzes each of the wavelength ranges associated with the various sensors 120 to determine a measurement for each sensor.

The embodiment shown in FIG. 5C is similar to the embodiment of FIG. 5A. Rather than using a single optical fiber for both downward-going and upward-going light, however, the embodiment of FIG. 5C separates the downward-going light path 44A from the upward-going light path 44B. Though both paths may be contained in a single fiber optic cable, the two light paths are carried on separate fibers. Light pulses from source 122 travel downward on path 44A, are distributed to the optical sensors 120 as provided previously, and reach the detector 124 via path 44B. Travel time differences will produce a series of light pulses at the detector, each pulse corresponding to a different optical sensor. Alternatively, or in addition, the optical sensors may operate in different wavelength bands and the sensor measurements may be distinguished accordingly. A similar modification can be made to the embodiment of FIG. 5B to return the light along a separate upgoing path.

In many cases, the well's temperature and pressure profile may be predictable enough that a distributed temperature/pressure sensing system is deemed unnecessary, and in such cases it may be omitted. Where such a system is deemed useful, the downhole optical sensor system 12 may further operate as a distributed temperature and/or pressure measurement system. Such systems are commercially available and may be modified to provide the chemical species sensing described above without sacrificing their ability to obtain distributed temperature and/or pressure measurements. Such systems may operate based on measurements of backscattered light from impurities along the length of the fiber. Such backscattered light has properties indicative of temperature and stress at the scattering location. The surface interface transmits light pulses and measures the properties of the backscattered light as a function of time. Combined with knowledge of the light's propagation velocity in the fiber, such measurements can be readily converted to position-dependent measurements of pressure and temperature. These measurements may be made on the optical fibers coupling the surface interface to the downhole optical sensors, or they can be made on separate optical fibers provided within cable 44. Where separate fibers are used, an additional light source and detector can be employed, or the existing source and detector may be switched periodically between the fibers.

The multi-measurement fiber optic cable may, for example, be deployed in a borehole along a fluid flow path (e.g., cable 44 in FIG. 4) such that the fiber optic cable experiences the same temperature and/or pressure as fluid flowing in the well. A surface interface (e.g., the surface interface 42 of FIG. 1) may transmit light pulses into the optical fibers and collect measurements for use by a scale/corrosion measurement system.

FIG. 6 is a flowchart of a method 140 for operating a well (e.g., the well 10 of FIG. 1 or FIGS. 3-4). During a first block 142 of the method 140, one or more downhole optical sensors (e.g., the optical sensor 40 of FIG. 1 or FIGS. 3-4, or the optical sensors 120 of FIGS. 5A-5C) are deployed in a fluid flow path (e.g., the formation fluid 28 of FIG. 1) in the well. Concurrently or separately, a distributed temperature sensor and/or a distributed pressure sensor may be deployed in the well during block 144. During a block 146, the downhole optical sensor(s) are probed from the surface interface (e.g., the interface 42 of FIG. 1 of FIGS. 3-4) to detect the concentrations of one or more chemical species. In block 148, a scale/corrosion measurement system (e.g., computer 60 of FIG. 1) derives a rate or quantity of scale buildup or corrosion based on the detected concentrations and, where applicable, the measurements from the distributed temperature and pressure sensor(s). Some alternative embodiments may, rather than predicting a scaling/corrosion rate, instead provide an estimated useful life remaining for the well. Such a life estimate can be based at least in part on combining the chemical species measurements over time with the relevant parameters of the well (fluid type, flow path diameter, tubing composition, bottom hole pressure, etc.) and experimentally derived time-to-failure measurements based on scaling or corrosion phenomena.

One or more corrective actions are taken in optional block 150 if the derived rate of scale buildup or corrosion is determined to be excessive. The corrective actions may include, for example, adjusting one or more fluid flow rates, circulating one or more inhibitors (e.g., introducing scale inhibitors or corrosion inhibitors), and replacing tubular strings (e.g., the production string 24 of FIG. 1 and FIGS. 3-4). The probing during the block 146 and the deriving during the block 148 may be performed while a formation fluid flows along the flow path.

Numerous variations and modifications will become apparent to those skilled in the art once the above disclosure is fully appreciated. It is intended that the following claims be interpreted to embrace all such variations and modifications.

What is claimed is:

1. A downhole optical sensor system comprising:
   at least one optical sensor positioned in a borehole and coupled to an interface via a fiber optic cable attached to an exterior of a casing string or production tubing in the borehole;
   a computer coupled to the interface;
   wherein each of the optical sensors comprises:
      a waveguide for conducting light; and
      a reagent region positioned between the waveguide and a fluid in the borehole to absorb a portion of the light from the waveguide, wherein the reagent region comprises a reagent that complexes with a chemical species in the fluid, causing a change in an absorption spectrum of the reagent in dependence upon a concentration of the chemical species in the fluid,
   wherein the computer obtains measurements indicative of said concentration and derives a rate or quantity of scale buildup or corrosion on one or more metal surfaces within the borehole based at least in part on said measurements.

2. The system of claim 1, wherein the computer derives an estimated useful life of one or more casing string components based at least in part on said measurements.

3. The system of claim 2, wherein the computer comprises an output device that communicates to a user said estimated useful life.

4. The system of claim 2, wherein the computer derives the rate or quantity of scale buildup or corrosion on one or more metal surfaces within the borehole based on said measurements as well as predetermined temperature and pressure profiles for the borehole.

5. The system of claim 1, wherein the computer derives the rate or quantity of scale buildup or corrosion on one or more metal surfaces within the borehole based on said measurements being associated with inhibitors added to reduce scale buildup or corrosion on the one or more metal surfaces within the borehole.

6. The system as recited in claim 1, wherein the reagent comprises a chromoionophore that complexes with ions of at least one of: barium, calcium, iron, lead, magnesium, phosphorus, potassium, sodium, strontium, zinc, and a sulfur oxyanion.

7. The system as recited in claim 1, wherein the fiber optic cable comprises an optical fiber having a core surrounded by a cladding layer, wherein the waveguide comprises a portion of the core of the optical fiber, and wherein the reagent region comprises a portion of the cladding layer.

8. The system of claim 1, wherein the reagent region is in direct contact with the waveguide and the fluid.

9. The system of claim 1, wherein the interface comprises an optical port configured to provide light to each optical sensor via the fiber optic cable, and configured to receive altered light from each optical sensor.

10. The system of claim 9, further comprising:
    a light source configured to provide light to the optical port; and
    a detector configured to receive the altered light from each of the optical sensors and to produce measurements indicative of concentrations of the chemical species.

11. The system as recited in claim 9, wherein the system comprises multiple optical sensors positioned at different locations along the fiber optic cable.

12. The system as recited in claim 11, wherein the fiber optic cable conveys a pulse of the source light to each of the optical sensors and receives a reflected pulse of light from each of the optical sensors, and wherein the interface receives the reflected pulses of light from the optical sensors at different times.

13. The system as recited in claim 11, wherein the source light includes multiple frequency bands, and wherein each of the optical sensors is active in a different one of the frequency bands, and wherein the fiber optic cable conveys the source light to each of the optical sensors and provides reflected light from each of the optical sensors to the interface.

14. A method for operating a well, comprising:
    deploying one or more downhole optical sensors in a fluid flow path along an exterior of a casing string or production tubing in the well, each of the one or more downhole optical sensors having a waveguide for conducting light and a reagent region between the waveguide and a fluid of the fluid flow path, wherein the reagent region comprises a reagent for complexing with a chemical species in the fluid, causing a change in an absorption spectrum of the reagent in dependence upon a concentration of the chemical species in the fluid;
    probing the one or more downhole optical sensors from a surface interface to detect concentrations of one or more chemical species; and
    deriving a rate or quantity of scale buildup or corrosion on one or more metal surfaces within the well based at least in part on the detected concentrations.

15. The method of claim 14, further comprising:
    deploying at least one of a distributed pressure sensor and a distributed temperature sensor in the well, wherein said deriving is based at least in part on measurements from the distributed pressure sensor or distributed temperature sensor.

16. The method of claim 14, wherein said probing and deriving is performed while fluid from a formation flows along the flow path.

17. The method of claim 14, further comprising taking corrective action if the derived rate or derived quantity is determined to be excessive.

18. The method of claim 17, wherein the corrective action includes at least one of: adjusting a fluid flow rate, treating with an inhibitor, treating with a scale removal fluid, and replacing tubular fluid conduits.

* * * * *